United States Patent [19]

Stortroen et al.

[11] 4,374,491
[45] Feb. 22, 1983

[54] APPARATUS FOR TREATING AND DISPOSING OF BIO-HAZARDOUS WASTE AND SOLID WASTE

[76] Inventors: Don J. Stortroen; Michael L. Brown, both of P.O. Box 1183, Tracy, Calif. 95376

[21] Appl. No.: 215,836

[22] Filed: Dec. 12, 1980

[51] Int. Cl.³ .......................................... B30B 15/30
[52] U.S. Cl. ............................. 100/73; 100/215; 100/245; 100/229 A; 422/26; 422/300
[58] Field of Search .............. 100/73, 74, 75, 70 R, 100/71, 45, 215, 229 A, 245; 422/26, 291, 300

[56] References Cited

U.S. PATENT DOCUMENTS

| | | | |
|---|---|---|---|
| 3,547,577 | 12/1970 | Lovercheck | 100/70 R |
| 3,691,648 | 9/1972 | Kraus | 100/73 X |
| 3,831,514 | 8/1974 | Jernstrom | 100/70 R |
| 3,926,107 | 12/1975 | Dunlap | 100/73 X |
| 3,948,167 | 4/1976 | De Feudis | 100/215 |

FOREIGN PATENT DOCUMENTS

| | | | |
|---|---|---|---|
| 2505185 | 8/1976 | Fed. Rep. of Germany | 422/26 |
| 54-109261 | 8/1979 | Japan | 100/215 |
| 1346262 | 2/1974 | United Kingdom | 100/73 |
| 2004020 | 3/1979 | United Kingdom | 422/26 |

*Primary Examiner*—Billy J. Wilhite
*Attorney, Agent, or Firm*—Harris Zimmerman; Howard Cohen

[57] ABSTRACT

An apparatus for neutralizing and disposing of infectious solid waste and non-hazardous solid waste includes a housing having an upper chamber for receiving the infectious solid waste and a lower chamber for receiving the non-hazardous solid waste. The upper chamber includes an exterior loading door, and an interior discharge door. A discharge ram forms one wall of the upper chamber opposite to the discharge door. The upper chamber includes door seals and pressure fittings so that the infectious waste placed therein may be sterilized by steam introduced under pressure. The neutralized wastes are ejected by the discharge ram through the interior door into the lower chamber. One wall of the lower chamber comprises a compactor ram which is extendable through a discharge opening to compress the neutralized and non-hazardous wastes into a closed compactor container.

4 Claims, 8 Drawing Figures

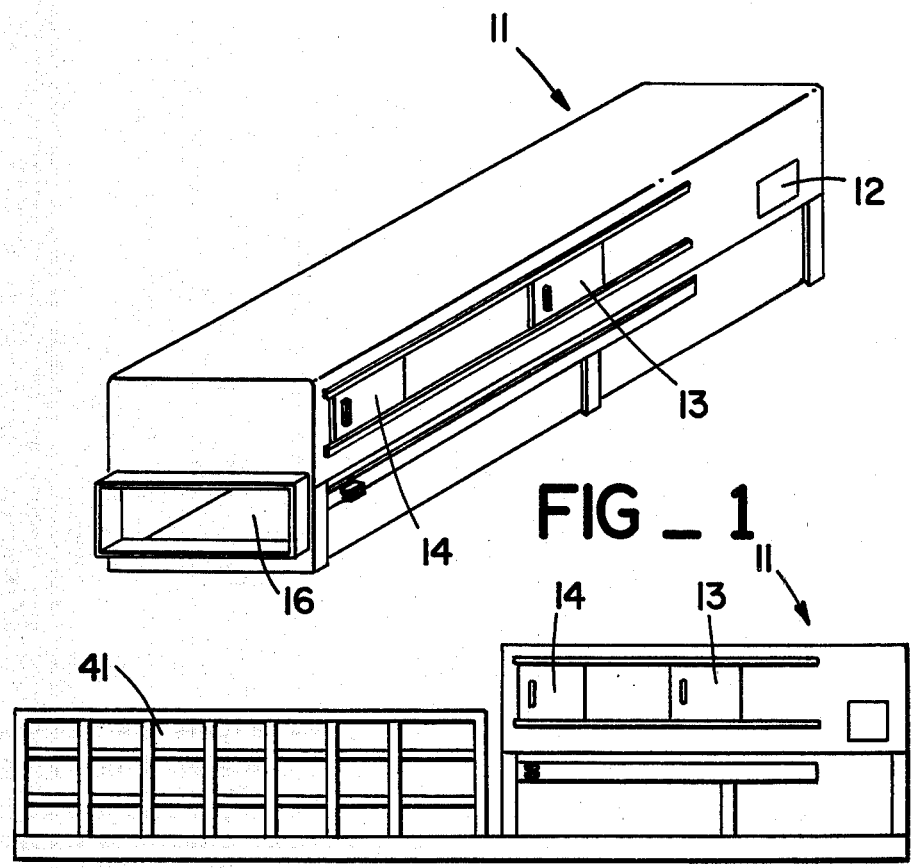
FIG_1
FIG_2
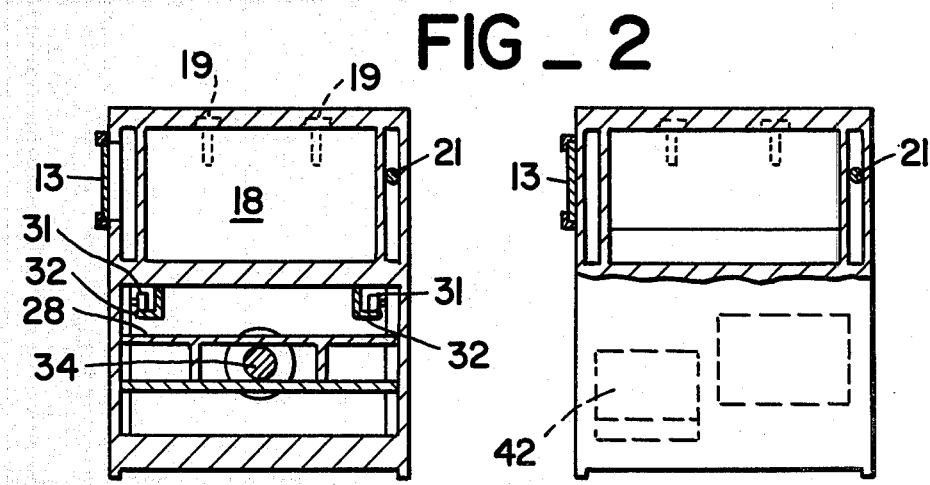
FIG_3
FIG_4

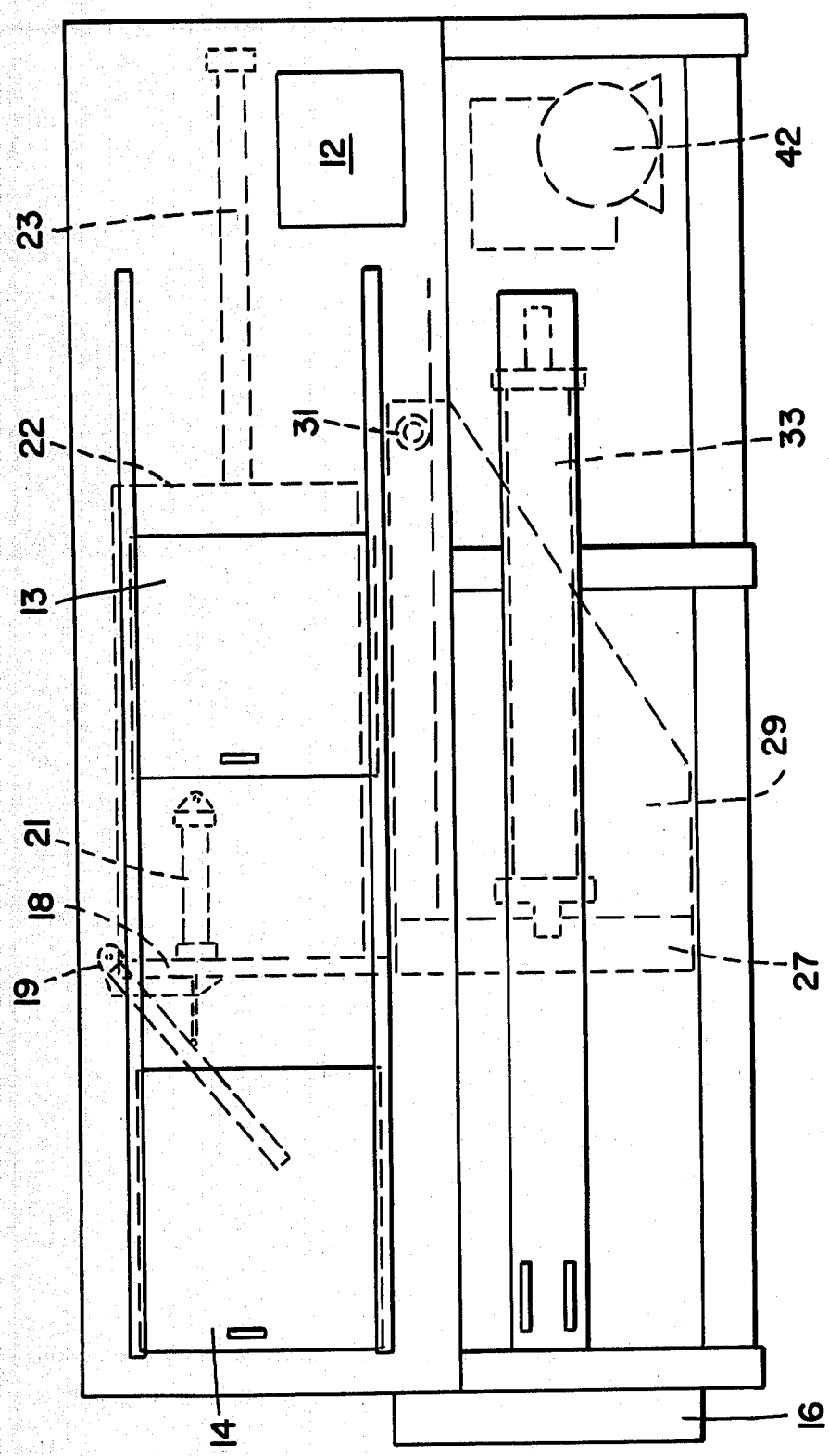
FIG_5

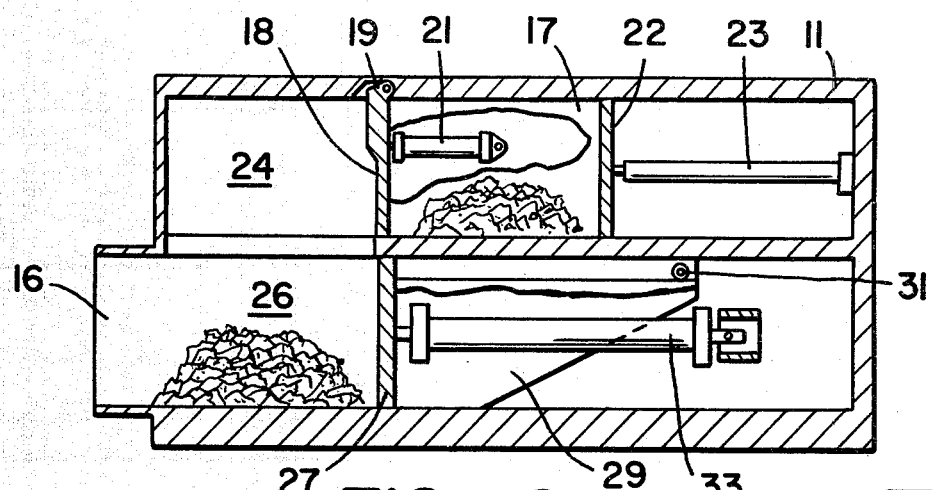
FIG_6
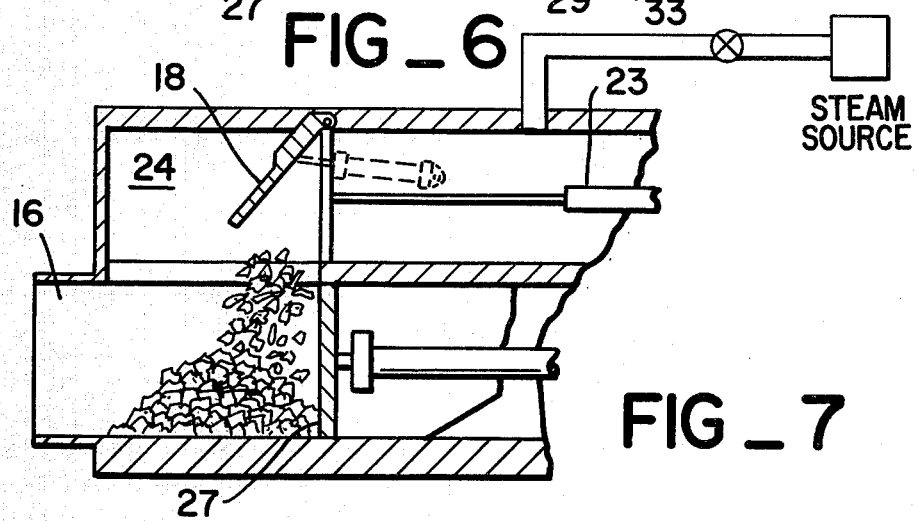
FIG_7
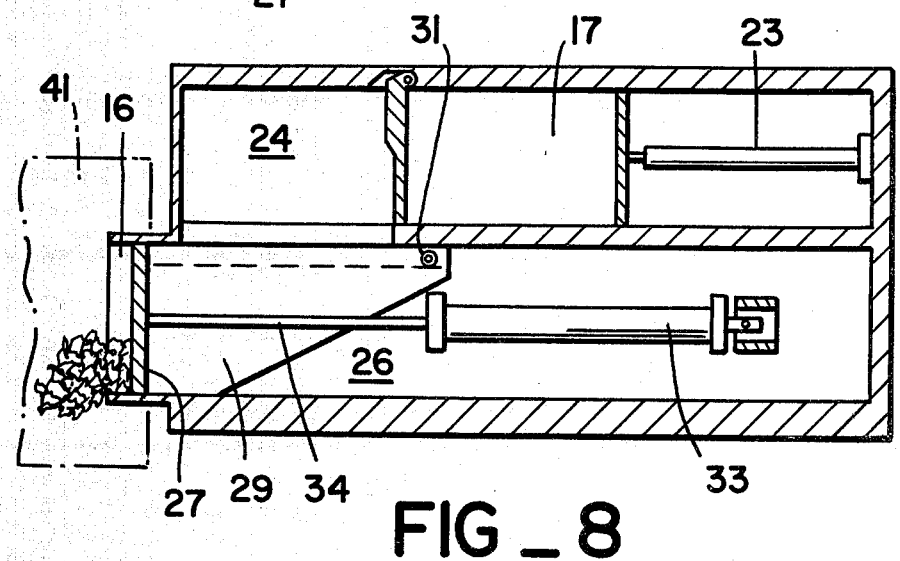
FIG_8

APPARATUS FOR TREATING AND DISPOSING OF BIO-HAZARDOUS WASTE AND SOLID WASTE

BACKGROUND OF THE INVENTION

The management and disposal of solid waste material generated by medical institutions and treatment facilities has become increasingly problematic in recent years. A significant portion of this solid waste material contains infectious micro-organisms and other hazardous biological materials which require special handling and disposal techniques.

In the past, the simplest solution to the problem of disposal of bio-hazardous wastes has been to incinerate these wastes and thereby destroy both the wastes and the contaminating micro-organisms. Incinerators installed for this purpose are commonly found in medical institutions.

In recent years, several new factors have made the incineration of bio-hazardous waste an undesirable option. The bio-hazardous wastes are not very combustible, due to their high water content and their high content of quasi-combustible materials such as plastics, artificial fibers, and the like. As a result, complete incineration of bio-hazardous materials requires a substantial fuel input to achieve temperatures sufficient to render total the combustion of the wastes. The steep increases in fuel costs in recent years have greatly increased the operating cost of an incinerator. These costs are likely to increase significantly in the near future.

Another development in recent years is the increased concern over air quality, and the new laws and regulations governing the discharge of pollutants into the air. Many existing incinerators cannot meet the current pollution emission standards, and must be retro-fitted with scrubbers to remove pollutants from the stack gases of the incinerator. Scrubber devices and retro-fitting of existing installations can be an extremely expensive undertaking. Further increases in the stringency of the pollution emission standards may have the practical effect of outlawing incinerators, even when they are equipped with scrubber units.

Furthermore, an incinerator equipped with a stack gas scrubber is a sophisticated mechanism which requires a licensed operator or engineer to be in attendance on a continuing basis. Thus, modern incinerators involve not only high capital outlays initially, but also high fuel costs and high labor costs as well. In addition, incinerators produce ash and soot which create their own handling and disposal problems.

It is common procedure to operate an incinerator only when solid waste has accumulated sufficiently to warrant operation, especially in light of the high rate of fuel consumption of most incinerators. Thus, it is necessary to store temporarily the solid wastes and infectious, bio-hazardous wastes which are to be incinerated. Storage of the bio-hazardous wastes further increases the possibility of malfactors escaping therefrom, due to the extra handling steps which are necessitated by temporary storage.

Faced with these growing problems deriving from incineration of bio-hazardous and solid wastes, many medical institutions are looking for cheaper, safer, and more practical methods of solid waste management and disposal.

SUMMARY OF THE PRESENT INVENTION

The present invention generally comprises an apparatus which is designed to neutralize and dispose of bio-hazardous wastes and non-hazardous solid wastes, especially those generated by medical institutions and treatment facilities. Compared to prior art techniques, the apparatus of the present invention requires far less energy input, emits no air pollutants whatsoever, provides a safe temporary storage area for bio-hazardous wastes, and substantially reduces the total volume of disposed wastes.

The apparatus comprises a generally rectangular housing having an upper chamber adapted to receive and store bio-hazardous and infectious solid wastes, and a lower chamber adapted to receive and store non-hazardous solid wastes. The upper chamber includes an intake door opening externally of the housing, as well as a discharge door which opens internally in the housing. The side of the chamber opposite the discharge door comprises a movable wall which is translatable by an hydraulic piston. The walls and doors of the upper chamber are provided with pressure seals so that the chamber may retain steam under pressure. The steam, which may be provided externally by an existing steam line commonly available at medical institutions, is introduced into the upper chamber for a period of time to sterilize the contents thereof. Subsequently, the discharge door is opened and the opposing wall is translated to discharge the contents of the upper chamber into the lower chamber.

The lower chamber also includes an intake door which opens exteriorly of the housing. One wall of the lower chamber is provided with a port which is in open communication with a closed compactor container. The wall of the lower chamber opposite the port comprises a compactor ram which is translatable by a second hydraulic cylinder. Solid wastes of the non-hazardous variety may be stored in the lower chamber, to which is added the neutralized solid wastes which are discharged from the upper chamber. When the lower chamber is full, the compactor ram may be actuated to compress the accumulated wastes in the chamber and push them through the port into the compactor container. The compaction process reduces the volume of solid waste by a factor of seven or more. When the compactor container is filled, it may be transported to a land-fill site and emptied.

A BRIEF DESCRIPTION OF THE DRAWING

FIG. 1 is a perspective view of the waste disposal apparatus of the present invention.

FIG. 2 is a side elevation of the apparatus of the present invention.

FIG. 3 is a cross-sectional elevation of the apparatus as shown in FIG. 2.

FIG. 4 is a cross-sectional view of the apparatus as shown in FIG. 2.

FIG. 5 is a side elevation of the apparatus of the present invention.

FIG. 6, FIG. 7, and FIG. 8 are cross-sectional side elevations of the apparatus of the invention, showing the sequential operation thereof.

DESCRIPTION OF THE PREFERRED EMBODIMENT

The present invention generally comprises an apparatus for treating and neutralizing infectious bio-hazardous solid wastes, and disposing of these neutralized wastes along with other non-hazardous solid wastes. As shown in FIGS. 1–5, the apparatus includes a large rectangular housing 11 having on one side a control panel door 12 adjacent to one end of the housing. Disposed on the same side of the housing is a door 13 disposed medially in the side and a door 14 disposed adjacent to the other end of the housing. As shown in FIG. 1, the other end of the housing includes a discharge port 16.

Within the housing there is situated a chamber 17 which is adapted to receive infectious and other bio-hazardous solid wastes. The chamber 17 is disposed in the upper medial portion of the housing 11, and access to the chamber 17 is through the door 13. The chamber 17 is generally rectangular, having fixed, opposed side walls and top and bottom walls. However, the end wall 18 of the chamber 17 is supported by hinges 19 at the upper edge thereof to form an internally opening discharge door for the chamber 17. The door is rotated from the closed position (FIG. 6) to the open position (FIG. 7) by means of an hydraulic cylinder 21. The cylinder 21 is secured to the frame of the housing 11 adjacent to the side opposite the door 13 of the chamber 17. The translatable piston of the cylinder 21 is pivotally secured to the hinged panel 18 to effect rotation thereof, as shown also in FIG. 5.

The end wall of the chamber 17 opposite the end wall 18 comprises a translatable ram 22 which is selectively translatable by means of an hydraulic cylinder 23, as shown in FIGS. 5–8. The ram 22, the hinged wall 18, and the external door 13 are all provided with pressure sealing fittings so that the chamber 17 may retain elevated gas pressure. Furthermore, as schematically illustrated in FIG. 7, an external source of pressurized steam is connected through appropriate controls and valves in the housing 11 to the chamber 17. With the ram 22 retracted, as shown in FIG. 6, and with the doors 13 and 18 closed, pressurized steam may be introduced into the chamber 17 to heat and sterilize the contents of the chamber. The steam heating procedure is controlled by automatic devices known in the prior art and capable of monitoring the temperature and timing of the steam heating cycle.

Directly adjacent to the hinged wall 18 is an antechamber 24 which provides clearance for the panel 18 to rotate upwardly therein. Directly below the antechamber 24 is a compaction chamber 26. The exterior door 14, which is provided for the intake of non-hazardous solid wastes, opens directly to the antechamber 24, which is in open communication with the compaction chamber 26. Thus, the non-hazardous solid wastes which are received in the apparatus through the door 14 enter the antechamber 24 and fall directly into the compaction chamber 26. Likewise, it may be appreciated that the sterilized wastes from the chamber 17 which are ejected by the ram 22 into the antechamber 24 also fall into the compaction chamber 26.

The compaction chamber 26 includes side walls and a bottom wall which are disposed in rectangular relationship. One end wall of the chamber 26 is provided with a discharge port 16. The wall opposite the port 16 is formed by a compactor ram 27. The rear face of the compactor ram 27 includes laterally extending reinforcing members 28 as shown in FIG. 3. A pair of trapezoidal panels 29 extend rearwardly from the side edges of the ram 27. Joined to the upper edges of the panels 29 are a plurality of rollers 31. The rollers are supported on longitudinally extending, L-shaped track members 32, as shown in FIG. 3. The ram is thus supported by the rollers 31 on the track 32 to facilitate reciprocal translation of the ram.

The ram 27 is translated by means of an hydraulic cylinder 33 extending longitudinally in the housing 11 beneath the chamber 17 and the hydraulic cylinder 23. The piston rod 34 of the hydraulic cylinder 33 is secured to a medial portion of the ram 27, as shown in FIG. 3.

The apparatus of the present invention is designed to operate cooperatively in association with a closed compactor container 41, as shown in FIG. 2. The compactor container 41, which is known in the prior art, is a reinforced, closed, rectangular container having a single opening in one end thereof, to which the discharge port 16 is designed to mate. Thus, all of the refuse processed by the apparatus of the present invention is discharged through the port 16 directly into the closed container 41, without any manual handling.

It may be noted that the housing 11 also includes therein an hydraulic pump 42 which supplies the hydraulic cylinders 23 and 33. Automatic controls known in the prior art are also provided for the pump 42.

To employ the apparatus of the present invention, all infectious and bio-hazardous wastes are placed in the chamber 17 by means of the exterior door 13. In the chamber 17, the hinged wall 18 is closed and the ram 22 is retracted, as shown in FIG. 6. The chamber 17 has a substantial volume, on the order of 3.5 cubic yards, so that a great amount of bio-hazardous wastes may be placed in the chamber 17. Furthermore, the bio-hazardous wastes may be placed in the chamber 17 as they are created, so that the chamber 17 also serves as an isolated storage area for the bio-hazardous solid wastes.

Likewise, the chamber 26 may be used to store non-hazardous solid wastes as they are created, the solid wastes being introduced therein through the exterior door 14. Thus, the apparatus of the present invention serves an important waste storage function, as well as treatment and disposal of the wastes.

When the chamber 17 is substantially filled with bio-hazardous solid wastes, steam under pressure is introduced therein to heat the bio-hazardous wastes and effect sterilization thereof. For example, a typical sterilization cycle may require one half hour to fill the chamber 17 with steam, heat the contents to approximately 250°, and vent the steam externally. This process is controlled by automatic timers and sensors.

After the steam cycle is completed, the hinged wall 18 is pivoted to the open position by the hydraulic cylinder 21. The ram 22 is then extended, as shown in FIG. 7, thereby pushing all of the sterilized waste from the chamber 17 into the antechamber 24. The sterilized waste falls into the compactor chamber 26, where it mingles with the non-hazardous solid waste placed there previously. When the chamber 26 is full of waste, or at any other time when it is convenient or necessary, the ram 27 is advanced by the hydraulic cylinder 33. The waste accumulated in the chamber 26 is thus driven through the discharge port 16 into the compactor container 41, as shown in FIG. 8. The hydraulic cylinders 21, 23, and 33 may then be retracted to return the apparatus to its loading configuration. The preferred embodiment of the present invention is used in conjunction with a closed compactor container 41, known in the prior art and having a capacity of approximately 18 cubic yards. When this container is full, it holds the equivalent of approximately 120–130 cubic yards of non-compacted waste. The full container may be removed from the site of the apparatus 11, transported to a land-fill site or the like, emptied, and returned to the apparatus.

It should be emphasized that the apparatus of the present invention discharges absolutely no pollutants into the atmosphere or environment. Furthermore, operation of the present invention is fully automatic, and may be accomplished by maintenance or housekeeping personnel. The cost of operating the apparatus is approximately 28 cents per hour, compared to incinerator operating costs of approximately $5.00 to $10.00 per hour. Thus the present invention represents a substantial improvement over prior art hazardous and non-hazardous waste disposal methods.

We claim:

1. Apparatus for receiving, treating, and disposing of bio-hazardous or infectious solid wastes and non-hazardous or non-infectious solid wastes, comprising a housing defining a pair of discrete separate adjacent chambers, the first of said chambers being enclosed and having an opening therein through which infectious waste may be introduced, said first chamber being adapted to permit steaming and sterilization of the infectious waste, the second of said chambers being enclosed and having an opening therein through which non-infectious material may be introduced, means defining a passage interconnecting said first and second chambers, a closure for selectively opening and closing said passage, means for ejecting the sterilized contents from said first chamber into said second chamber through said passage when said closure is in an open position, and compaction means in said second chamber for selectively compacting the non-infectious waste and for compacting the infectious waste received from said first chamber and for ejecting all of such waste from said housing at one end of said second chamber.

2. Apparatus as set forth in claim 1 in which said compaction means comprises a ram extending across said second chamber, said second chamber end has a discharge opening, and said ram is translatable towards said discharge opening and away from the same.

3. Apparatus as set forth in claim 1 in which said first chamber overlies said second chamber and said passage permits gravital deposit of said sterilized waste from said first chamber to said second chamber, and said ejection means includes a ram translatable towards and from said passage.

4. Apparatus as set forth in claim 3 in which said passage overlies said second chamber adjacent said discharge opening.

* * * * *